United States Patent [19]

Martens, III et al.

[11] 4,320,873
[45] Mar. 23, 1982

[54] CONTROLLED RELEASE AIR FRESHENER USING AN ABSORBENT GENERATOR

[75] Inventors: Edward J. Martens, III; Phillip J. Neumiller, both of Racine County, Wis.

[73] Assignee: S. C. Johnson & Son, Inc., Racine, Wis.

[21] Appl. No.: 40,807

[22] Filed: May 21, 1979

[51] Int. Cl.$^3$ .......................... A61K 7/46; A61L 9/04; A61L 13/00
[52] U.S. Cl. .......................... 239/6; 239/54; 239/60; 252/522 R; 424/16; 424/19; 424/76
[58] Field of Search .......... 239/6, 54, 60; 424/16, 424/76, 19; 252/522

[56] References Cited

U.S. PATENT DOCUMENTS

| | | | |
|---|---|---|---|
| 2,927,055 | 3/1960 | Lanzet | 424/76 |
| 3,016,199 | 1/1962 | Keydel | 239/55 |
| 3,303,091 | 2/1967 | MaiLander et al. | 424/76 |
| 3,688,985 | 9/1972 | Engel | 239/54 |
| 3,969,280 | 7/1976 | Sayce et al. | 424/76 |
| 4,051,159 | 9/1977 | Tsoucalas et al. | 239/54 |
| 4,067,824 | 1/1978 | Jeng et al. | 424/76 |
| 4,071,616 | 1/1978 | Bloch | 424/76 |

FOREIGN PATENT DOCUMENTS

865425 3/1978 Belgium.
1517410 7/1978 United Kingdom.

OTHER PUBLICATIONS

McCutcheon's Detergents & Emulsifiers 1971 Annual pp. 30, 35 and 91.

*Primary Examiner*—Allen J. Robinson

[57] ABSTRACT

A method for controlling the rate of evaporation or rate of release of a perfume from an absorbent substrate in a continuous action air freshener comprising incorporating into the perfume from 10 to 900% by weight based on the weight of the perfume of a vapor control agent selected from the group consisting of nonionic surfactants having an average of from 1 to 5 moles of ethylene oxide per molecule, a compound having the structure:

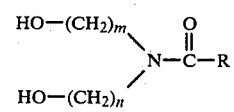

wherein m and n are intigers, the same or different, selected from 1 to 4, and R is an alkyl group having from 12 to 18 carbon atoms, a compound having the structure:

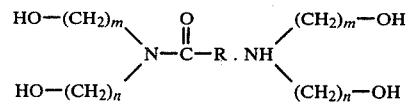

wherein m and n are intigers, the same or different, selected from 1 to 4, and R is an alkyl group having from 12 to 18 carbon atoms, and mixtures thereof. The use of the above agents controls the rate of release of volatile perfumes from absorbent substrates so as to prevent the premature evaporation of the perfumes to provide acceptable product life.

9 Claims, No Drawings

CONTROLLED RELEASE AIR FRESHENER USING AN ABSORBENT GENERATOR

BACKGROUND OF THE INVENTION

This invention relates to a method of controlling the rate of release of perfumes from continuous action air fresheners and more particularly to controlling the rate of release of perfumes from continuous action air fresheners having cellulosic substrates as the perfume reservoir and generator.

Continuous action air fresheners are slow diffusers which release perfume into an environment at a relatively controlled rate over an extended period of time to impart a desirable perfume to cover or mask undesirable odors which may be present. There have been numerous materials described as reservoirs for continuous action air fresheners. Some of these reservoirs such as carrageenin gels as disclosed in U.S. Pat. No. 2,927,055, metal crosslinked carboxymetyl cellulose gels as disclosed in U.S. Pat. No. 3,969,280 and amylose gels as described in U.S. Pat. No. 4,071,616 inherently release perfume over an extended period of time as the gel evaporates or sublimes into the atmosphere. There also have been attempts to control the release of perfumes from cellulosic substrates such as described in Belgian Pat. No. 865,425 which utilizes specific nonionic surfactants, namely, octyl and nonyl phenols having relatively high degree of ethoxylation and British Pat. No. 1,517,410 which describes the use of polyethylene or another plastic film to surround a cellulosic substrate to control the rate of release of the perfume from the substrate.

The various carrageenin, CMC and amylose gels, although effective as continuous action air fresheners are somewhat difficult to prepare and all have some form of syneresis present in the product. Furthermore, these gels typically have a useful life of 21–30 days. Furthermore, these products are heavy because of the high water content and must be protected from freezing as the gels generally are not freeze-thaw stable.

On the other hand the products using cellulosic substrates as reservoirs and generators as typified by the above-noted Belgian and British patents offer certain advantages over the gel-type forms. However, the structure as exemplied by the above-noted British patent is difficult to package because the plastic or polyethylene film wrapper is permeable to the perfume. When this package is sealed in an outer impermeable package, the perfume diffuses through the inner package to form a damp or wet surface on the film when the package is opened. This can be solved by using various ampoules to contain the perfume, however, this also has some disadvantages. The use of a vapor retardant as taught in the Belgian patent acts to slow down the perfume without requiring artificial barriers and the like. The particular vapor retardants described in this patent do not control the rate of release of the perfume to an acceptable degree for extended product life.

U.S. Pat. No. 3,016,199 contains a general disclosure of the use of nonionic surfactants similar to those taught in the Belgian patent in combination with cellulosic substrates and perfumes.

It has now been discovered, however, that certain surfactants having a particular critical degree of ethoxylation have superior vapor retardant properties as compared to the nonionic surfactants generally disclosed in Belgian Pat. No. 865,425 and U.S. Pat. No. 3,016,199.

SUMMARY OF THE INVENTION

It has been unexpectedly found that certain nonionic surfactants having a particular molecular weight and degree of ethoxylation are superior in controlling the rate of release of perfumes from absorbent substrates. The use of from 10 to 900% by weight based on the weight of the perfume of these certain surfactants flattens out or controls the weight loss of perfume from the absorbent substrate to the air. These surfactants are nonionic surfactants having a degree of ethoxylation of 5 moles of ethylene oxide or less, and certain amides or super amides. Also mixtures of these materials may be utilized.

OBJECTS AND ADVANTAGES

It is the primary object of the present invention to provide an improved method for controlling the rate of release of perfumes from absorbent substrates.

It is a further object of the present invention to provide an inexpensive and effective method for preparing slow diffusing continuous action room air freshener devices.

It is a still further object of the present invention to provide a method for utilizing cellulose as an inexpensive yet effective reservoir and generator for volatile perfumes.

It is a still further object of the present invention to improve the fragrance profile of perfumes generated from cellulosic substrates.

Still further objects and advantages of the present invention will become more apparent from the following more detailed description thereof.

DETAILED DESCRIPTION OF THE INVENTION

The method of the present invention for controlling the rate of release of a volatile perfume from an absorbent substrate in which the perfume has been impregnated in a continuous action air freshener comprises incorporating into the perfume from 10 to 900% by weight based on the weight of the perfume of a vapor-control agent selected from the group consisting of nonionic surfactants having an average of from 1 to 5 moles of ethylene oxide per molecule, a compound having the formula

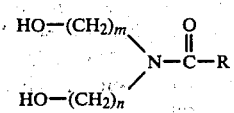

wherein m and n are intigers, the same or different, selected from 1 to 4 and R is an alkyl group having from 12 to 18 carbon atoms, a compound having the formula

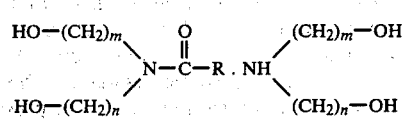

wherein m and n are intigers, the same or different, selected from 1 to 4, and R is an alkyl group having from 12 to 18 carbon atoms, and mixtures thereof; incorporating the perfume and the vapor control agent into the absorbent substrate the absorbent substrate including from 2 to 20 grams of the perfume.

When used in the instant specification and in attached claims, the term "cellulosic substrate" refers to a fibrous, woven or non-woven, substrate formed from a cellulosic material such as cotton, paper, cardboard, pulp, and the like, in a relatively flat sheet form. This term does not refer to and does not include carboxymethylcellulose gels as described in U.S. Pat. No. 3,969,280.

Any absorbent substrate can be utilized as the substrate in the method of the present invention. The substrate should be sufficiently absorbent so as to absorb sufficient perfume and vapor-control agent without appreciable free moisture which would give a wet or damp surface. The substrates should be sufficiently absorbent to absorb from 50 to 500% by weight, based on the weight of the substrate, of perfume and vapor-control agent. It is preferred that the substrate be sufficiently absorbent to absorb 100 to 400% by weight, based on substrate weight, of perfume and vapor-control agent. The density of the substrate is not particularly critical; however, it is preferred that the substrate have a bulk density within the range of from about 0.15 g/cc to 1.0 g/cc and preferably 0.20 g/cc to 0.60 g/cc.

Suitable substrates include cotton batting, cotton fiber based non-woven substrates, including filter substrates, wood pulp sheets such as pulp sheets formed from prehydrolysed Kraft hardwoods, sulfated pine and other soft woods and the like. Highly absorbent papers are suitable as are synthetic non-woven materials such as polyester felts, sintered polyethylene and other absorbent substrates. Other similar absorbent substrates are suitable so long as the absorbency and density are within the above ranges.

Although any of the above-noted substrates can be used in the method of the present invention, cellulosic substrates are preferred. Furthermore, the following cellulosic substrates are particularly preferred: cotton based non-woven filter substrate, sulfated pine pulp and absorbent paper. Each of the above substrates are commercially available materials.

Furthermore, the absorbent substrate can be substantially any size or shape. The only requirement being that sufficient surface area is exposed or can be exposed to the atmosphere to release the perfume. These air fresheners can be arranged or stored in various dispensing devices such as described in U.S. Pat. Nos. 3,964,684, or 4,077,183 or within a device such as described and claimed in co-pending application Ser. No. 4,104, filed Jan. 17, 1979 now U.S. Pat. No. 4,220,281. Other suitable package designs which sufficiently afford the large surface area can be utilized.

As the perfumes used in the continuous action air fresheners, almost any perfume designed for use in continuous action air fresheners which is available from a commercial perfumer can be utilized. Typically, perfumes are complex proprietary mixtures of ingredients to provide a specific scent or fragrance. Perfumes generally are described in terms of their vapor characteristics and in terms of the notes or fragrances which the perfumes emit. Suitable perfume classes for the use in the continuous action air fresheners of the present invention include floral perfumes, such as rose, various flower garden mixtures, lavender, and the like, various citrus fragrances including lemon, lime, citrus mixtures, and the like, various evergreen or outdoor fragrances such as pine, spruce, and the like; various herb or spice fragrances, such as cinnamon, vanilla, strawberry, etc. Substantially any fragrance can be used utilized in the method of the present invention so long as the fragrance is compatible with the substrate chosen.

As noted earlier, perfumes available from commercial perfume suppliers generally are mixtures of various ingredients which have various components which evaporate or vaporize at different rates. By controlling the rate of evaporation of the more quickly evaporating materials, the profile of the perfume can be altered to improve the fragrance and extend the effective life of the perfume. Generally it is desirable to have the perfume have an initial lift of fragrance which provides an initial impression of fragrance which is then continued on in the less volatile substances. The choice of a particular perfume is up to the taste of the individual user. The amount of perfume used is a matter of choice. Generally from 2 to 20 grams of perfume is incorporated into each generator.

In order to slow down or control the evaporation or release of the perfumes from the absorbent substrate, it is necessary to incorporate a vapor-control agent. If the perfumes are merely impregnated or incorporated into the absorbent substrate without the use of a vapor-control agent, the perfumes quickly evaporate within a period of one or ten days after the package is opened. However, by utilizing vapor-control agents and particular utilizing the vapor-control agents described and claimed in the instant method, it is possible to extend the use and usable lifetime of these perfumes from an absorbent substrate to a period of from 30 to 60 days. Of course, the useful life of a generator is highly dependent on the amount and type of perfume incorporated into the substrate as well as the amount and type of vapor-control agent.

Furthermore, it has been found that the vapor-control agents used in the present invention improve the fragrance profile of aged perfume which are impregnated in cellulosic substrates. These vapor control agents appear to inhibit rapid volatilization of the lighter fractions in the perfume so that the perfume plus vapor-control agent is preferred over perfume alone.

It has been found that from 10 to 900% by weight, based on the weight of the perfume, the vapor-control agent can be incorporated into the perfume. It is preferred that the vapor-control agent be present in an amount of from 50 to 300% by weight, based on the weight of the perfume. It is most preferred to incorporate from 75 to 200% by weight, based on the weight of the perfume, of the vapor-control agent.

The first class of vapor-control agents useful in the method of the present invention are the nonionic surfactants having an average of from 1 to 5 moles, and preferably 1 to 3 moles, of ethylene oxide per molecule. These nonionic surfactants fall into a number of general classes of nonionic surfactants such as the octyl and nonyl phenol ethoxylates, the straight chain alcohol ethoxylates, the branch chain ethoxylates and the like. The only criterion with regard to the nonionic surfactants be that the nonionic surfactants each have an average degree of ethoxylation of from 1 to 5 moles of ethylene oxide per molecule. This excludes the use of higher ethoxylates such as described in the Belgian Pat. No. 782,565, which do not function as efficiently or as effectively as these lower ethoxylate nonionic surfactants. Specific nonionic surfactants which are usable in the method of the present invention include the following:

the octyl phenols having an average of one to five moles of ethylene oxide such as the Triton X series from Rohm and Haas, nonyl phenols having an average of one to five moles of ethylene oxide such as the Surfonic N series from Jefferson Chemicals, the primary alcohol etholylates such as the Neodol series from Shell Chemicals, and the secondary alcohol ethoxylates such as the Tergitol S series from Union Carbide and the like. Certain specific nonionic surfactants include: octyl phenol+1.0 EO, octyl phenol+3.5 EO, octyl phenol+4.5 EO, nonyl phenol+1 EO, nonyl phenol+4 EO, mixed $C_{12}$-$C_{15}$ alcohols+3 EO, mixed $C_{12}$-$C_{13}$ alcohol+3 EO, mixed $C_{12}$-$C_{15}$ alcohol+5 EO, mixed $C_{12}$-$C_{15}$ secondary alcohol+3 EO, mixed $C_{12}$-$C_{15}$ secondary alcohol+5 EO, stearic acid+5 EO.

A second class of surfactants usable as a vapor-control agent in the present invention are the di-lower alkyl, i.e. having 1 to 4 carbon atoms, alcohol fatty amides. These materials are exemplified by the following formula:

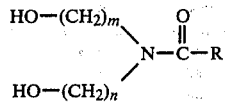

wherein m and n are intigers and can be the same or different selected from 1 to 4, and R is an alkyl group having from 12 to 18 carbon atoms. It is preferred that the lower alkyl group be the same and the preferred lower alkyl group is ethyl. With regard to the higher alkyl group it is preferred that this alkyl group be selected from the following groups: dodecaryl, tetradecaryl, hexadecaryl, octadecaryl and mixtures such as produced from coco acids and other natural mixtures. The most preferred alkyl group is lauryl. Suitable amides include diethanol amide laurate, diethanol amide palmitate, diethanol amide stearate, dimethanol amide laurate, dipropanol amide laurate, dibutanol amide laurate. Furthermore, the preferred amides of this class are the diethanol amide laurate.

A third class of compounds are related to this second group of compounds and are described as superamides. These complex compounds are thought to have the following co-ordinate formula:

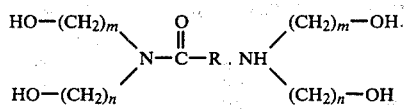

wherein m and n are intigers and can be the same or different, preferably the same, selected from 1 to 4, and R is a alkyl group having from 12 to 18 carbon atoms. The preferred values for m and n are 2 while the preferred values for the alkyl group are the lauryl, coco and stearyl, with lauryl being the most preferred.

Preferred vapor-control agents are the nonyl phenols plus 1 to 5 EO groups, octyl phenols plus 1 to 5 EO groups, the dialkanol amides laurates. The most preferred are the octyl and nonyl phenols plus 1 to 3 EO groups.

The vapor-control agents can be incorporated into the perfume by simple mixing technique prior to the impregnating or incorporation of the perfume, vapor-control agent into the substrate. It is necessary to hermetically seal the impregnated or treated absorbent substrate until the container is used to prevent premature perfume loss. Suitable methods of such sealing are well known in the art and need not be described here.

The method of the present invention will be fully described by the following examples wherein all parts and percentages are by weight and all temperatures and degrees Celcius. These examples shall in no way be construed as limiting the scope of the subject matter of the present invention.

EXAMPLE 1

A mixture of 6 grams of a floral perfume and 4 grams of Surfonic N-10, a nonyl phenol+1 EO nonionic surfactant were impregnated into J-5 pads having 42 in² surface area from Filter Materials. The pad is placed in a dispenser as disclosed in U.S. application Ser. No. 004,104, filed Jan. 17, 1979. As a control 6 grams of the same perfume on the same substrate material was placed in an identical package. The packages were exposed to the atmosphere at room temperature and the weight loss were measured at various intervals as shown in Table I.

TABLE I

| No. of Days | Control Grams Lost | Example 1 Grams Lost |
|---|---|---|
| 1 | 1.50 | 1.06 |
| 2 | 1.87 | 1.36 |
| 5 | 2.28 | 1.66 |
| 6 | 2.47 | 1.83 |
| 7 | 2.71 | 2.01 |
| 13 | 3.27 | 2.46 |
| 14 | 3.48 | 2.63 |
| 16 | 3.63 | 2.70 |
| 19 | 3.77 | 2.77 |
| 20 | 3.90 | 2.89 |
| 22 | 4.16 | 3.06 |
| 34 | 4.80 | 3.53 |
| 35 | 4.79 | 3.46 |
| 37 | 4.99 | 3.62 |
| 44 | 5.22 | 3.81 |
| 47 | 5.42 | 4.01 |
| 51 | 5.39 | 4.03 |
| 55 | 5.49 | 4.15 |
| 58 | 5.54 | 4.22 |
| 65 | 5.62 | 4.40 |

As is apparent from Table I, the addition of the specific nonionic surfactant reduced the loss of perfume to the atmosphere. The sample without surfactant lost over one-half the perfume in 13 days while 22 days were required for the mixture of Example 1.

EXAMPLE 2

A mixture of 4 grams of a rose perfume oil was mixed with 6 grams of nonyl phenol+1 EO. The mixture was impregnated into a 3.25"×4.50"×0.160" sheet of J-5 paper from Filter Materials, weighing 10.69 grams. The sheet was exposed to the air at room temperature and the weight loss was recorded at various intervals. In the control, 4 grams of the same perfume was impregnated in a similar paper weighing 11.00 grams. The results are shown in Table II.

TABLE II

| No. of Days | Control Grams Lost | Example 2 Grams Lost |
|---|---|---|
| 1 | 0.86 | 0.52 |
| 2 | 1.49 | 0.90 |
| 3 | 1.98 | 1.20 |
| 6 | 2.13 | 1.19 |
| 7 | 2.20 | 1.21 |
| 10 | 2.40 | 1.34 |

TABLE II-continued

| No. of Days | Control Grams Lost | Example 2 Grams Lost |
|---|---|---|
| 13 | 2.62 | 1.51 |
| 14 | 2.70 | 1.56 |
| 16 | 2.75 | 1.57 |
| 28 | 3.11 | 1.95 |
| 31 | 3.30 | 2.17 |
| 34 | 3.33 | 2.27 |
| 38 | 3.27 | 2.26 |
| 45 | 3.31 | 2.46 |
| 52 | 3.49 | 2.74 |
| 59 | 3.52 | 2.86 |
| 70 | 3.51 | 3.03 |

As is apparent from the Table, the modified perfume of Example 2 was much more controlled taking 31 days to lose 2.17 grams while the perfume alone lost 2.13 grams in 6 days. This clearly shows control.

EXAMPLE 3

Some 4.0 grams of lemon perfume oil was mixed with 4.0 grams of a nonyl phenol plus 1 EO nonionic surfactant. The mixture and a control using only 4.0 grams of the same lemon perfume were impregnated in 3.25"×4.50"×0.160" sheets of Filter Materials J-5 paper. Example 3 and the control were exposed to the air at room temperature. The weight loss data is shown in Table III.

TABLE III

| Days | Example 3 Grams Lost | Control Grams Lost |
|---|---|---|
| 2 | 2.40 | 2.87 |
| 3 | 2.51 | 3.07 |
| 6 | 2.75 | 3.29 |
| 7 | 2.85 | 3.32 |
| 9 | 2.86 | 3.33 |
| 21 | 3.08 | 3.38 |
| 24 | 3.17 | 3.44 |
| 27 | 3.22 | 3.49 |
| 31 | 3.24 | 3.38 |
| 38 | 3.34 | 3.41 |

EXAMPLE 4

Some 5.0 g of a lemon perfume oil was mixed with 7.50 g of nonyl phenol plus 1 EO nonionic surfactant. This was impregnated in a 3.25"×4.50"×0.160" sheet of Filter Materials J-5 paper. The weight loss data is shown in Table IV. Although there is no control, the weight loss data has a flatter curve than other controls.

EXAMPLE 5

Example 4 was repeated except that 7.50 g of Superamide 100 CG, a coconut diethanolamide superamide was used in place of the nonionic surfactant. The weight loss data is shown in Table IV. This surfactant provided better control than the nonionic of Example 4.

TABLE IV

| | Example | |
|---|---|---|
| Days | 4 Grams Lost | 5 Grams Lost |
| 1 | 3.14 | 3.18 |
| 2 | 3.53 | 3.40 |
| 5 | 3.84 | 3.50 |
| 7 | 3.96 | 3.53 |
| 9 | 4.02 | 3.56 |
| 16 | 4.26 | 3.71 |
| 23 | 4.40 | 3.87 |
| 30 | 4.37 | 3.84 |
| 40 | 4.43 | 3.87 |
| 44 | 4.47 | 3.86 |
| 58 | 4.54 | 3.98 |

COMPARATIVE EXAMPLES 1–3

Three nonyl phenol ethoylates having more than 5 moles of ethylene oxide were mixed with four grams of lemon perfume oil. In each instance 6 grams of nonionic was used. The mixtures were impregnated on a 4.25"×4.50" sulfatate H-J pulp. The weight loss data is shown as Table VI.

TABLE VI

| Comp. Ex. | 1 | 2 | 3 | Control |
|---|---|---|---|---|
| Moles of Ethylene Oxide | $6_1$ | $8.5_2$ | $30_3$ | — |
| Days | Wt. Loss G. | Wt. Loss G. | Wt. Loss G. | Wt. Loss G. |
| 2 | 2.99 | 3.06 | 3.11 | 3.63 |
| 14 | 3.40 | 3.44 | 3.56 | 3.74 |
| 17 | 3.46 | 3.49 | 3.61 | 3.75 |
| 21 | 3.60 | 3.66 | 3.75 | 3.85 |
| 23 | 3.64 | 3.68 | 3.78 | 3.87 |

$_1$Surfonic N-60
$_2$Surfonic N-85
$_3$Igepol CO-880

Although the higher ethoxylates retarded perfume evaporation somewhat, the rate is higher than the lower ethoxylates.

EXAMPLE 6 AND COMPARATIVE EXAMPLE 4

Some 5.0 gms of the perfume oil of Example 3 mixed with 7.5 grms of nonyl phenol+3 EO nonionic surfactant was impregnated on a 3.25"×4.50"×0.160" sheet of Filter Materials J-5 paper. This pad was placed inside a molded polyethylene package having adjustable openings. The openings were opened fully. As a comparison, 5.0 gms of the same perfume was mixed with 7.5 gms of nonyl phenol. The weight loss data is shown below:

| Days | Example 6 Grams Lost | CE 4 Grams Lost |
|---|---|---|
| 1 | 2.32 | 2.58 |
| 2 | 3.03 | 3.17 |
| 3 | 3.22 | 3.34 |
| 6 | 3.52 | 3.65 |
| 7 | 3.66 | 3.82 |
| 8 | 3.66 | 3.83 |
| 9 | 3.73 | 3.87 |
| 10 | 3.68 | 3.87 |
| 13 | 3.82 | 3.84 |
| 14 | 3.92 | 4.12 |
| 15 | 3.97 | 4.16 |
| 16 | 3.98 | 4.17 |
| 17 | 3.86 | 3.99 |
| 20 | 4.04 | 4.23 |
| 21 | 4.06 | 4.24 |
| 22 | 4.14 | 4.32 |
| 27 | 4.09 | 4.26 |
| 28 | 4.13 | 4.32 |

EXAMPLE 7 AND COMPARATIVE EXAMPLE 5

Some 5 grams of a rose perfume were mixed with 3.33 grams of nonyl phenol plus 1 mole EO nonionic surfactant. The mixture was impregnated on a 3.25"×4.50"×0.160" sheet of Filter Materials J-5 paper. In Comparative Example 5 only 5.0 grams of the same perfume was impregnated on the paper. Each paper was aged 44 days in the atmosphere. The aged papers were presented to a panel of 7 people to determine which paper is preferred. All 7 indicated that the paper of Example 7 was preferred as having a stronger and better rose.

This indicates that the quality of the perfume is actually improved by the addition of the nonionic surfactant.

EXAMPLE 8

Example 7 was repeated using a lemon and a blend of perfumes characterized as a mixture of piney, herbal and citrus. For both the lemon and the blend the nonionic improved the perfume preferences after aging when compared to similar aged samples of the perfume not containing the nonionic.

We claim:

1. A method for retarding the rate of evaporation of a volatile perfume from an absorbent substrate in a continuous action air freshener comprising incorporating into the perfume from 10 to 900% by weight, based on the weight of the perfume, of a vapor-control agent selected from the group consisting of nonionic surfactants having an average of from 1 to 5 moles of ethylene oxide per molecule, and mixtures thereof.

2. The method of claim 1 wherein the vapor-control agent has an average of from 1 to 3 moles of ethylene oxide per molecule.

3. The method of claims 1 or 2 wherein the vapor-control agent is present in an amount of from 50 to 300% by weight based on the weight of the perfume.

4. The method of claims 1 or 2 wherein the vapor-control agent is present in an amount of from 75 to 200% by weight based on the weight of the perfume.

5. The method of claim 1 wherein the vapor-control agent is selected from the group consisting of nonyl phenol ethoxylates having an average of from 1 to 3 moles of ethylene oxide per molecule, octyl phenol ethoxylates having an average of from 1 to 3 moles of ethylene oxide per molecule and mixtures thereof.

6. The method of claim 1 wherein the vapor-control agent is nonyl phenol ethoxylate having one mole of ethylene oxide per molecule.

7. The method of claims 5 or 6 wherein the vapor-control agent is present in an amount of from 50 to 300% by weight based on the weight of the perfume.

8. The method of claims 5 or 6 wherein the vapor-control agent is present in an amount of from 75 to 200% by weight based on the weight of the perfume.

9. The method of claim 1 wherein the perfume is present in the substrate in an amount of from 3 to 15 grams.

* * * * *